United States Patent [19]
Schnipke et al.

[11] Patent Number: 6,158,205
[45] Date of Patent: Dec. 12, 2000

[54] GUIDE FOR INSERTING ARTICLES INTO CARTRIDGES

[75] Inventors: Leonard H. Schnipke; Ronald J. Schnipke; Donald K. Schnipke, all of Cloverdale, Ohio

[73] Assignee: Schnipke Family Limited Liability Company, Ottoville, Ohio

[21] Appl. No.: 09/353,096

[22] Filed: Jul. 14, 1999

Related U.S. Application Data

[60] Provisional application No. 60/108,560, Nov. 16, 1998.

[51] Int. Cl.$^7$ ............... B29C 37/02; B23Q 3/00
[52] U.S. Cl. .................. 59/71; 59/77; 29/464; 29/811.2; 29/138; 264/249; 227/110; 227/120; 227/176.1
[58] Field of Search ................... 29/464, 811.2; 264/138, 249; 59/71, 77; 227/110, 120, 176.1

[56] References Cited

U.S. PATENT DOCUMENTS

| | | |
|---|---|---|
| 3,751,902 | 8/1973 | Kingsbury et al. . |
| 3,894,174 | 7/1975 | Cartun . |
| 4,193,181 | 3/1980 | Boulanger et al. . |
| 5,392,509 | 2/1995 | Cheswick . |
| 5,653,928 | 8/1997 | Schnipke ............... 29/811.2 |
| 5,836,147 | 11/1998 | Schnipke ............... 59/71 |

*Primary Examiner*—David Jones
*Attorney, Agent, or Firm*—Francis T. Kremblas, Jr.

[57] ABSTRACT

An improved guide fixture is disclosed. The guide fixture includes two portions forming a guide passage. The first portion funnels a discrete element into a second portion. A knife edge located adjacent a slot in the guide passage separates the discrete element from a holder while the discrete element is inserted into a cartridge.

21 Claims, 11 Drawing Sheets

GUIDE FOR INSERTING ARTICLES INTO CARTRIDGES

CROSS-REFERENCES TO RELATED APPLICATIONS

This application claims the benefits o f U.S. Provisional Application No. 60/108,560 filed Nov. 16, 1998.

BACKGROUND OF THE INVENTION

1. Field of the Invention

The present invention relates generally to an apparatus and method for inserting discrete articles into cartridges. More particularly, the present invention relates to an improved fixture for use with properly inserting staple drivers into cartridges.

2. Description of the Related Art

In the field of microsurgery, a reusable surgical instrument is assembled in well-known conventional fashion where the cutting blade is mounted to traverse a specific pattern guided by elements of the surgical instrument. The blade and associated guide elements are mounted in somewhat remote location with respect to the hands of the surgeon. A conventional feature of the surgical instrument is a staple cartridge which is used only once.

The cartridge is a generally elongated rectangular plastic body which includes a channel formed longitudinally in an elongated body. The channel is a guide for the surgical blade which is secured on the surgical instrument. The structure of the instrument and cartridge which are well-known in the industry includes a plurality of small staples aligned in the cartridge parallel with the guide channel. After the blade makes its cut and other necessary surgical operations are performed, a remote actuator causes each side of the incision to be stapled together for obvious reasons.

The particular structure for manipulating the blade and actuating the staple operation is not a part of this invention and are well-known to one of ordinary skill in the art.

Due to the minute structure involved in the surgery for which this invention is made, there may be as many as fifty or more staples on each side of a two inch incision which are actuated simultaneously to close the wound. Because of the small size of the staples and the drivers in the cartridge for pushing the staples through the tissues against the anvil on the surgical instrument to deflect the points of the staple into a clasping position, the assembling of the drivers into the cartridge and maintaining them in place to drive the staples into the tissues is a labor intensive chore.

The prior art system for mounting the staple drivers in pockets in the cartridge is to form a plastic tree having aligned branches with staple drivers integrally formed on one end of each of the aligned branches. The already-formed conventional cartridge is placed in a fixture and the tree bearing the staple drivers is hand manipulated to place them adjacent the entrance to pockets in the cartridge. Each driver is pressed into the pocket in the cartridge by the fingers of the person doing the assembling. The separation of the individual drivers from the branch of the tree on which it is mounted is accomplished by a flexing of the branches of the tree manually to break off the staple drivers. Then, a hand-manipulated blade or prong is used to press each staple driver down into the cartridge to near the pocket opening on the opposite side of the cartridge.

Unfortunately, the finger operation of pressing each driver into a pocket, the flexing of the branches which also tilts the drivers and the subsequent pressing from the hand operated prongs can misalign some of the drivers within the pockets.

The size of the pockets and the periphery of the drivers may have a slight variation due to the minute structure involved and the fact that both the cartridge and the staple drivers are formed of thermoplastic resin, could cause some play in the assembly and that can cause an alignment problem. Particularly, an inversion of the cartridge could result in some drivers being displaced from their pockets due to gravity and/or impacts during assembly. Obviously, if the staple driver is not in place, there will be no staple at that point in the incision.

Another problem with the assembly is that of misalignment of the staple driver with the cartridge. The tree which holds the staple drivers is inserted into the passages on the fixture. The passages are funnel-shaped so as to attempt to more closely align an individual driver with an individual pocket on the cartridge. However, the use of the funnel-shaped passage does not fully cure the misalignment problem. Because the funnel does not fully engage the driver to be inserted, there is some potential for misalignment which still occurs.

The misalignment of the driver within the pocket can cause additional problems. If the driver is not properly aligned, the staple which is ejected by use of the staple driver may be inaccurately bent in use in surgery. In addition, the misalignment of the staple driver in the pocket can increase the force needed to eject a staple or prevent the activation of that staple entirely.

Yet another problem is the imprecision of separating the staple drivers from the branches of the plastic tree which is referred to as degating. There is a tendency for the remnant of the branch left on the staple driver to be of a random size and often the remnant is larger than desired. The staple drivers are attached to the holder before insertion into the cartridge, but must be removed from the tree before or during the insertion process. The separation of an individual staple driver from the tree leaves some material on a side of the staple driver. While it is not practical to remove all the branch material from the side of the staple driver in the separation process, it is important that the amount of material left on the side be relatively consistent between drivers. The material left on the side tends to cause friction when the staple driver is used in surgery. If the amount of material left is relatively consistent, it allows a user of such a staple cartridge to accurately predict the amount of force needed to expel a staple in surgery. In addition, the smaller the volume of material left, the less friction will be generated, and the less the force required to use the staple cartridge, which is beneficial in a surgical procedure.

SUMMARY OF THE INVENTION

The present invention relates to an apparatus for separating discrete elements from a holder and filling a cartridge with the discrete elements. The apparatus includes a cartridge, a guide fixture and a plurality of plungers.

The cartridge includes a plurality of pockets defined therein. Each pocket is configured to receive one discrete element.

The guide fixture includes a plurality of guide passages, a corresponding plurality of slots, and a corresponding plurality of knife edges. Each guide passage includes a first portion which has converging tapered walls and is configured to receive the one discrete element. Each guide passage also includes a second portion which is adjacent to and aligned with both the first portion and one of the pockets of the cartridge. Each second portion of the guide passage has walls which define a close fit relationship with the one discrete element as the discrete element passes along the length of the second portion, which tends to assure the desired orientation of the staple driver as it is inserted into the cartridge.

A plurality of slots are provided along a side of the guide fixture. Each slot extends a selected distance along the length of one of the guide passages. Each slot is configured to receive a branch portion of the holder. Each knife edge is disposed adjacent one of the slots and is configured to engage a holder portion near the discrete element after the discrete element has been inserted into the guide passage.

Each plunger is reciprocally mounted and aligned with a respective one of the guide passages. Each plunger is configured to force a discrete element through a guide passage and into a pocket of the cartridge. When the plunger contacts the discrete element and drives it through the guide passage, it also causes the holder portion near the discrete element to engage the knife edge and separate the discrete element from the holder.

The discrete elements may be staple drivers and the cartridge a staple cartridge. The second portion of the guide passage has a width which defines a close fit relationship with the discrete element, wherein preferably the width of the second portion is about 0.001 inch greater than the width of the discrete element. The length of the second portion of the guide passage is preferably about the same as the length of the discrete element. The tapered walls of the first portion terminate at an open lower end which has substantially the same size and shape as the opening in the upper end of the second portion.

The knife edge is oriented away from the cartridge and forms about a 45° angle with respect to the direction of travel of a discrete element through the guide passage. The knife edge is spaced a selected distance from the lower end of the guide fixture. This selected distance is about ½ the length of the discrete element.

The guide fixture may be made of a single part. Alternatively, the guide fixture may be made of two parts. The first portion of the guide passage may be formed in a first plate and the second portion of the guide passage may be formed in a second plate. The first plate may be secured to the second plate in any conventional fashion to align the first and second portions of the guide passages with one another.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other elements where such connection is recognized as being equivalent by those skilled in the art. Those skilled in the art will recognize that there are many, and in the future may be additional, alternative elements which are recognized as equivalent because they provide the same operations.

DETAILED DESCRIPTION OF THE INVENTION

Figure 1:
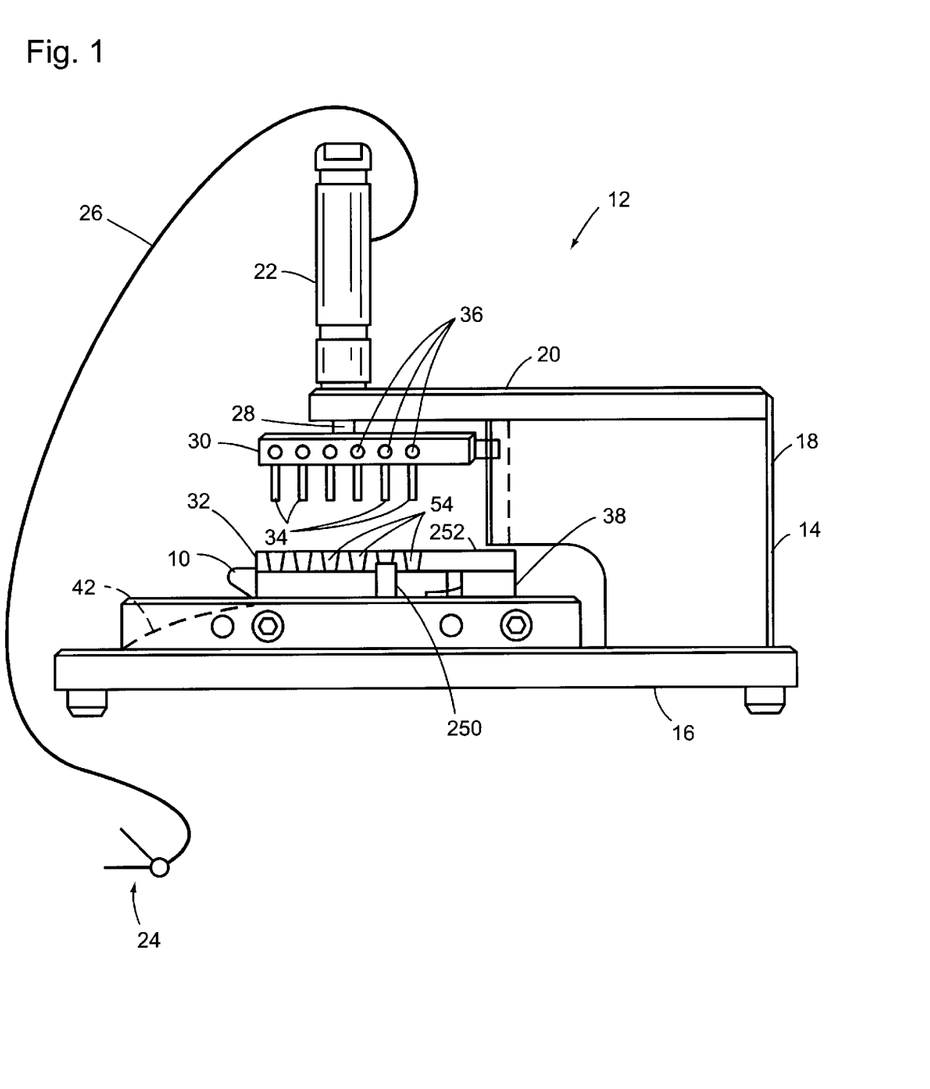
FIG. 1 is a side elevational view of an assembly apparatus for mounting staple drivers in a cartridge.

FIG. 1 illustrates apparatus for inserting staple drivers into pockets of a cartridge 10. The cartridge is of conventional structure and is molded or formed of a thermoplastic resin in conventional fashion.

Figure 2:
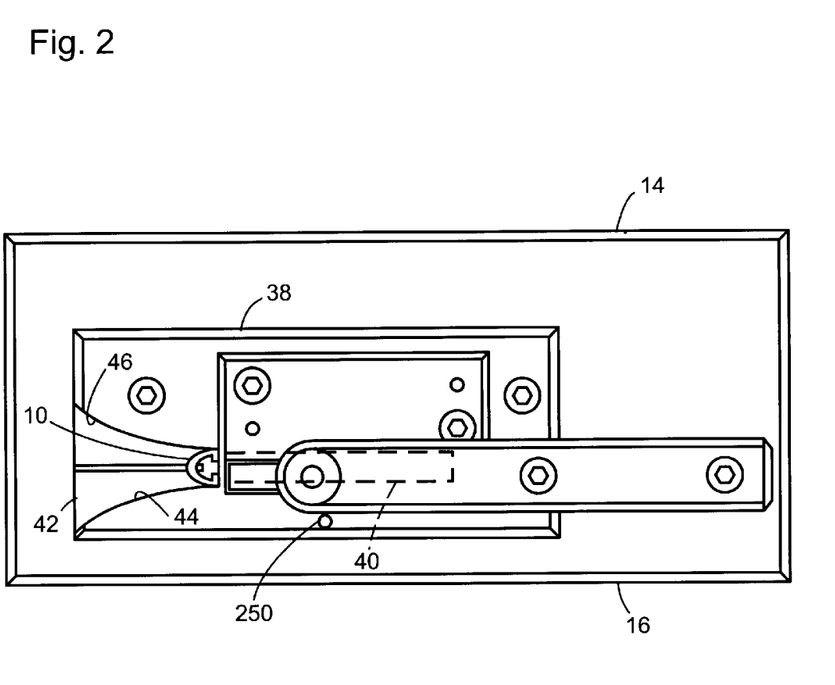
FIG. 2 is a top plan view of the apparatus of FIG. 1.

The apparatus of FIGS. 1 and 2, shown generally at 12 includes a framework 14 supported on a base 16 and having an upwardly projecting standard 18 with a forwardly projecting support arm 20. A piston and cylinder combination 22 is mounted above support arm 20 at the forward end thereof. The piston and cylinder combination 22 is illustrated schematically as being actuated by a foot pedal 24 connected to piston and cylinder combination 22 by line 26. Foot pedal 24 is in fact merely a switch which may be suitably connected to electric, pneumatic, or hydraulic systems to cause piston and cylinder combination 22 to reciprocate vertically.

A piston rod 28 projects from piston and cylinder combination 22 and is connected to a plate 30 by threads which may be used to adjust the spacing and length of the reciprocation stroke of the plate 30 with respect to a fixture 32 mounted below plate 30. A plurality of blade shaped plungers 34 are secured in holes (not illustrated) in the bottom of plate 30 and secured in place by set screws 36.

Figure 4:
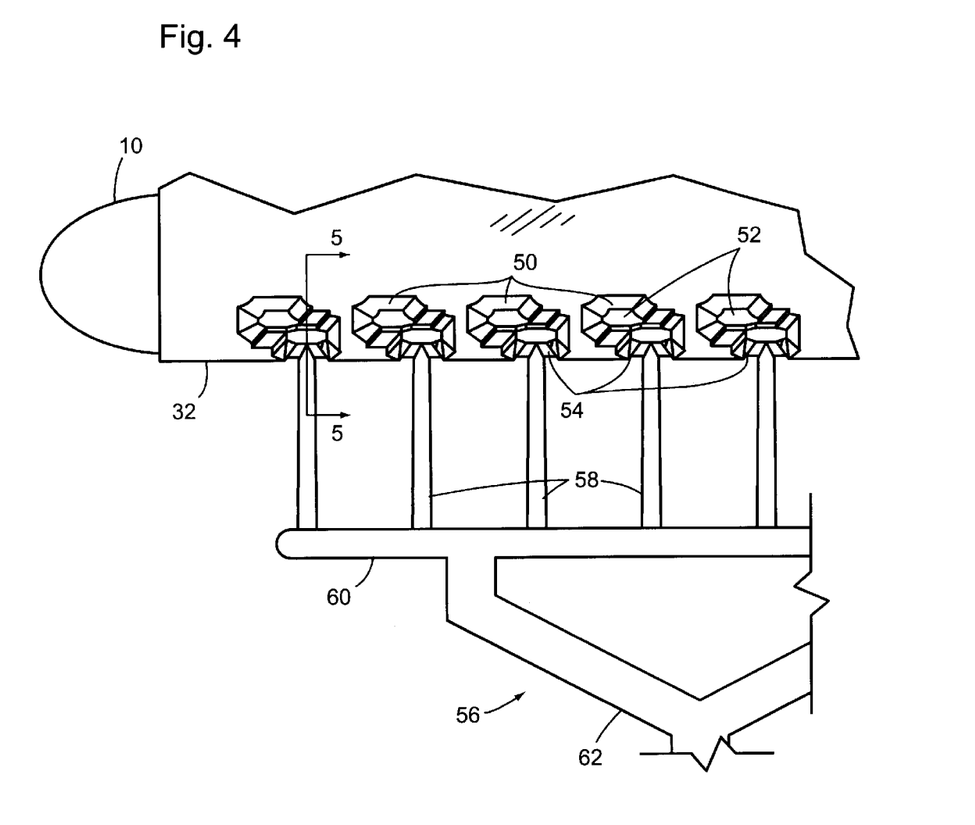
FIG. 4 is fragmentary sectional view taken along line 4—4 of FIG. 3.
Figure 5:
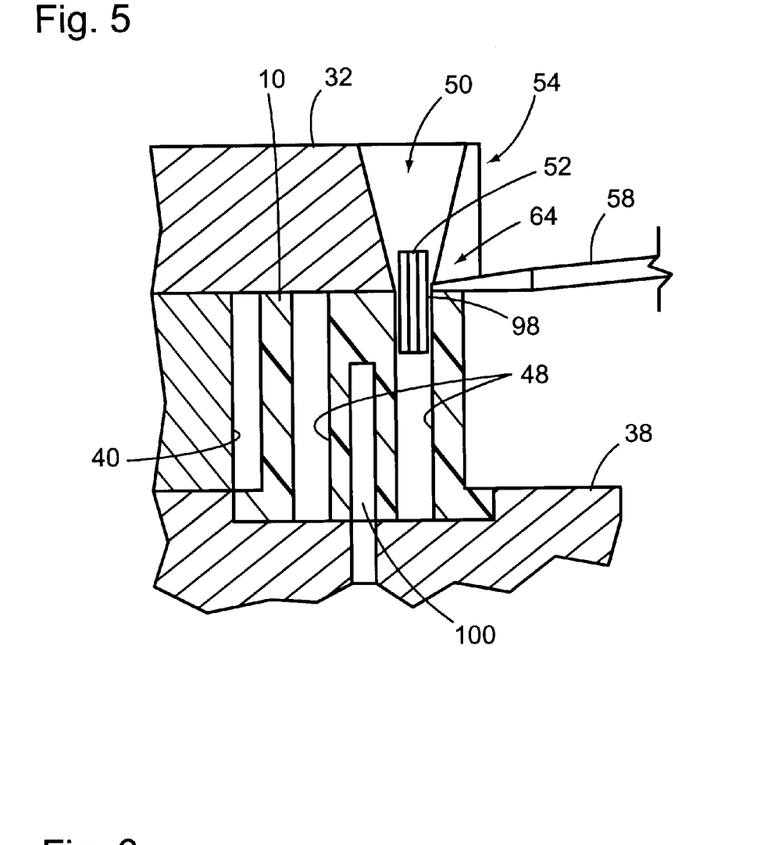
FIG. 5 is a fragmentary sectional view taken along line 5—5 of FIG. 4.

A support block 38 is secured on base 16 to provide a trough 40 which is configured to receive cartridge 10 between sloping converging walls 42,44,46, such that cartridge 10 cannot be inserted incorrectly and also such that pockets 48 in one side of cartridge 10 are vertically aligned with passages 50 formed in fixture 32. Note that each passage 50 extends vertically from the top of fixture 32 toward the bottom which is juxtaposed to cartridge 10 and as best seen in FIGS. 4 and 5, passages 50 are of a specific geometric shape to accommodate the shape of a double staple driver 52 as will be explained in more detail subsequently. Slots 54 extend through one side of fixture 32 for reasons which will also be explained subsequently.

Looking to FIGS. 3, 4, 5 and 6, a tree 56 formed of thermoplastic resin includes a plurality of branches 58 which are horizontally aligned with each other and project from a straight bar 60 connected to a trunk 62. The tree illustrated in FIG. 6 includes only a single molded double staple driver 52 for convenience. In normal practice, a double staple driver is integrally formed at one end of each branch 58 and connected thereto by a very narrow strip of plastic which may be broken to separate each driver 52 upon vertical bending of branches 58 with respect to drivers 52 when the drivers 52 are trapped in the exit or narrowest part 64 of converging passages 50 and the entrance opening to pockets 48, as best illustrated in FIG. 5. Other types of discrete elements may also be used in the present apparatus and method. For example, a single staple driver or other items which are inserted into a staple cartridge or other, similar cartridges using a similar type of holder may be inserted with the present apparatus and method.

An observation of FIG. 5 shows the staple drivers loosely mounted in the pockets 48 of the generally rectangularly shaped elongated cartridge 10. That is not really an accurate reflection of how they really work. There is very little play between the side walls of the pockets 48 and the periphery of the drivers 52 and they are configured in the preferred embodiment as a six-sided geometric configuration. Specifically, the six-sided element for driver 52 is depressed into the bottom part of pocket 48 near the generally six-sided pocket opening 98 by the plungers 34 when the piston and cylinder combination 22 is actuated manually by a foot, thigh or hand engaging the switch 24. The close tolerances between the lower or narrowest part 64 of passage 50 in fixture 32 and the close tolerance between the periphery of driver 52 and pocket opening 98 combine to keep and guide the driver into proper alignment upon its actuation at a later time when the cartridge is placed in operation as a replacement part in a surgical tool. The term "driver" is used interchangeably with the term "double driver" and the equivalent double driver has twelve sides fitting into two adjoining pockets. The concept remains the same.

Looking to FIG. 5, in operation, the cartridge 10 is ordinarily formed by injection molding using phenylene oxide of a specific color. Blue, red and other colors have specific meanings in the surgical field. The formation of the cartridge of elongated generally rectangular shape is conventional. It includes a guide channel 100 in one face to accommodate and guide a cutting blade which is actuated by other elements of the surgical instrument which is not relevant to this particular invention.

The incision made by the blade passing through guide channel 100 will later have its side edges stapled together by a plurality of staples (not illustrated) which are inserted into the cartridge through pocket openings 48. Each staple fits in a pocket 48 to be expelled by a driver 52 at a suitable time to be decided by a surgeon.

Figure 6:
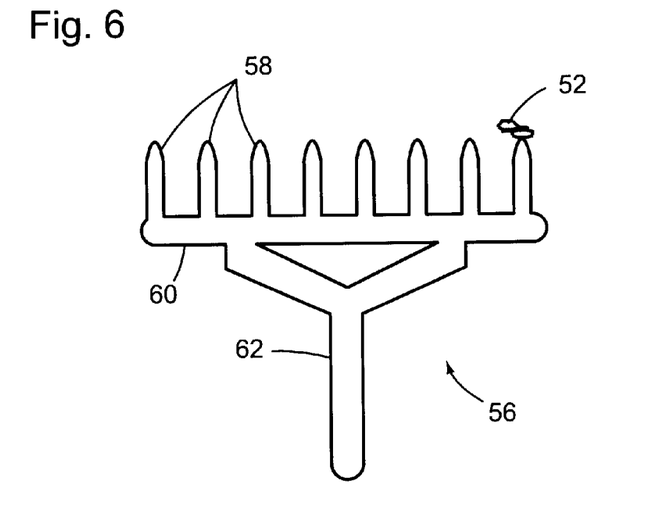
FIG. 6 is a top plan view of a tree with a plurality of branches and with a pair of staple drivers mounted on one end of one of the branches.
Figure 7:
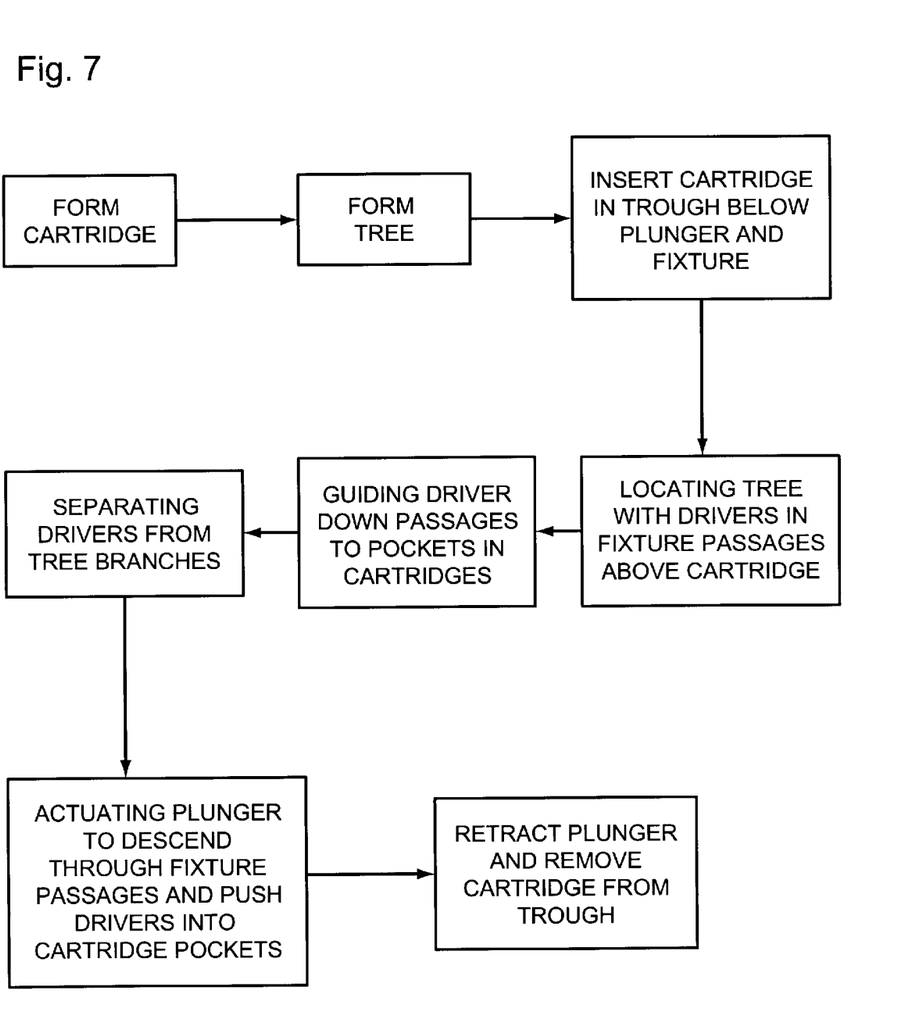
FIG. 7 is a block diagram of a procedural sequence of this invention.

A tree 56 illustrated in FIG. 6 is formed in conventional fashion with one or a double set of staple drivers 52 formed integrally with one end of each branch 58 of the tree.

The formed cartridge is inserted into a trough 40 (see FIGS. 3 and 5) below a plate 30. A fixture 32 is located intermediate the plate 30 and the cartridge 10.

Figure 3:
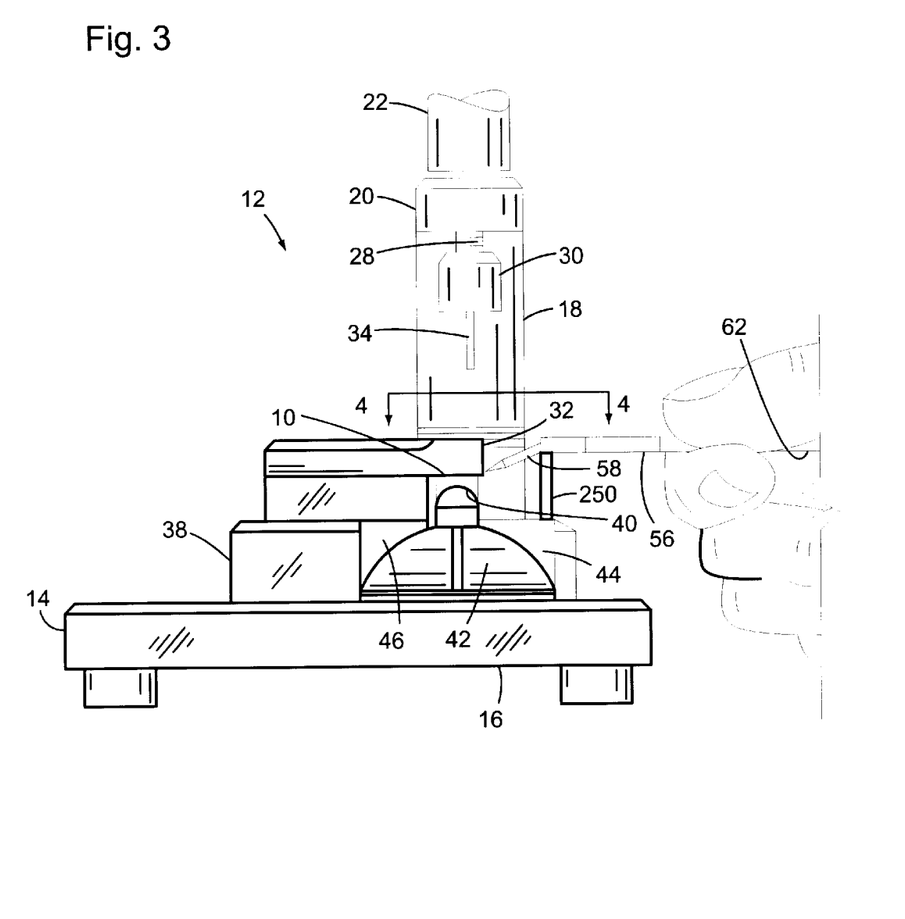
FIG. 3 is a left hand side elevational view of the apparatus of FIG. 1.

The tree 56 bearing the staple drivers 52 is hand manipulated such that the drivers slide into tapering passages 50 as illustrated in FIGS. 3, 4 and 5. It will be noted in FIG. 4 that the tapering converging passages 50 are of the same general geometric shape as the drivers mounted on the ends of branches 58. In the illustrated embodiment, a double set of drivers is mounted on each branch with the drivers being transversely offset with respect to each other and transversely of channel 100. In this instance, the double driver will drive two staples in tandem because the drivers are structured to move in tandem. It is clear that a single driver could be mounted in each pocket without any connection to any other driver.

Note that the narrow supporting portion of the branches 58 connected to the drivers slides downwardly in slots 54 until the branch 58 engages the upper surface of cartridge 10 (FIG. 5) with the driver 52 partially within the cartridge 10 and partially within the fixture 32. The narrow exit portion 64 of the fixture 32 closely surrounds the driver 52 such that it remains properly aligned in its geometric shape with the corresponding geometric shape of the pocket 48. Separation of the branches 58 from the drivers 52 is accomplished by raising and lowering the trunk 62 of the tree and wiggling it in a vertical plane to break the drivers from the branches while the throats 64 of the passages 50 and the pocket surfaces hold the driver in stationary position. A couple of bends accomplishes the desired separation.

After separation from branches 58, drivers 52 are pushed to near the bottom of pockets 48 by actuation of switch 24 which urges plunger plate 30 downward and the plungers 34 engage the trailing surfaces of drivers 52 to push them downward. The length of the plungers 34 and the thickness of the fixture 32 combine to serve as a stop in the downward passage of plungers 34 according to the desired result and this is accomplished by the threaded connection between plate 30 and piston rod 28.

A component of the cartridge includes an element which prevents more than one use of the cartridge in each surgical operation. Accordingly, the cartridge with the incorporated drivers and staples is a replacement part for a surgical instrument which involves a cutting blade. The remainder of the surgical instrument may be reused a plurality of times with replacement cartridges and perhaps with replacement cutting blades, but that does not relate to this particular inventive concept. The cartridge of this invention is a replaceable, one-time component which is replaced with each surgical procedure.

FIGS. 8 through 12 show an alternative and improved embodiment for the guide fixture 200. The remainder of the apparatus and method described above remains the same.

Figure 8:
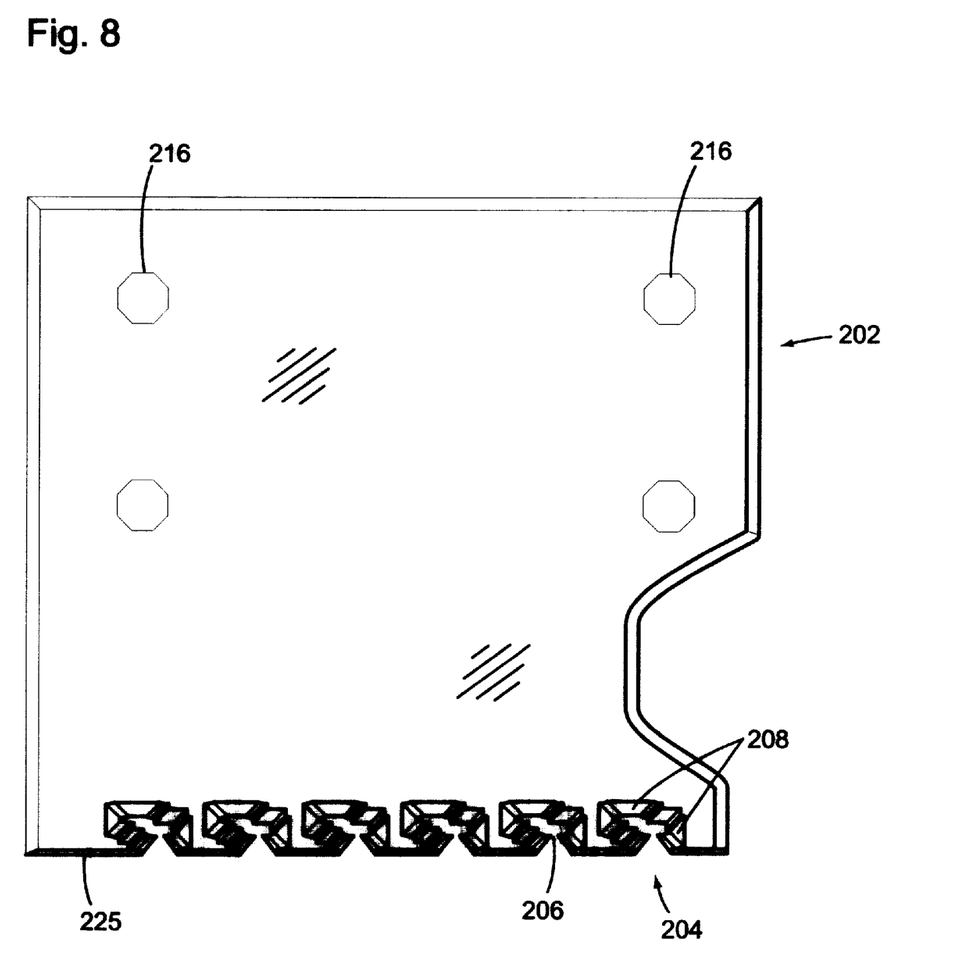
FIG. 8 is a top view of a first part of a guide fixture according to an alternative embodiment of the invention.

FIG. 8 illustrates a first plate 202 of the guide fixture 200. The first plate 202 of the guide fixture 200 includes a plurality of first portions 204 of guide passages 206. Each first portion 204 of a particular guide passage 206 is configured to receive one discrete element 52 as shown and described above. The first portions 204 have converging tapered walls 208 which are similar to the passages so described earlier with respect to FIGS. 1–7.

Figure 9:
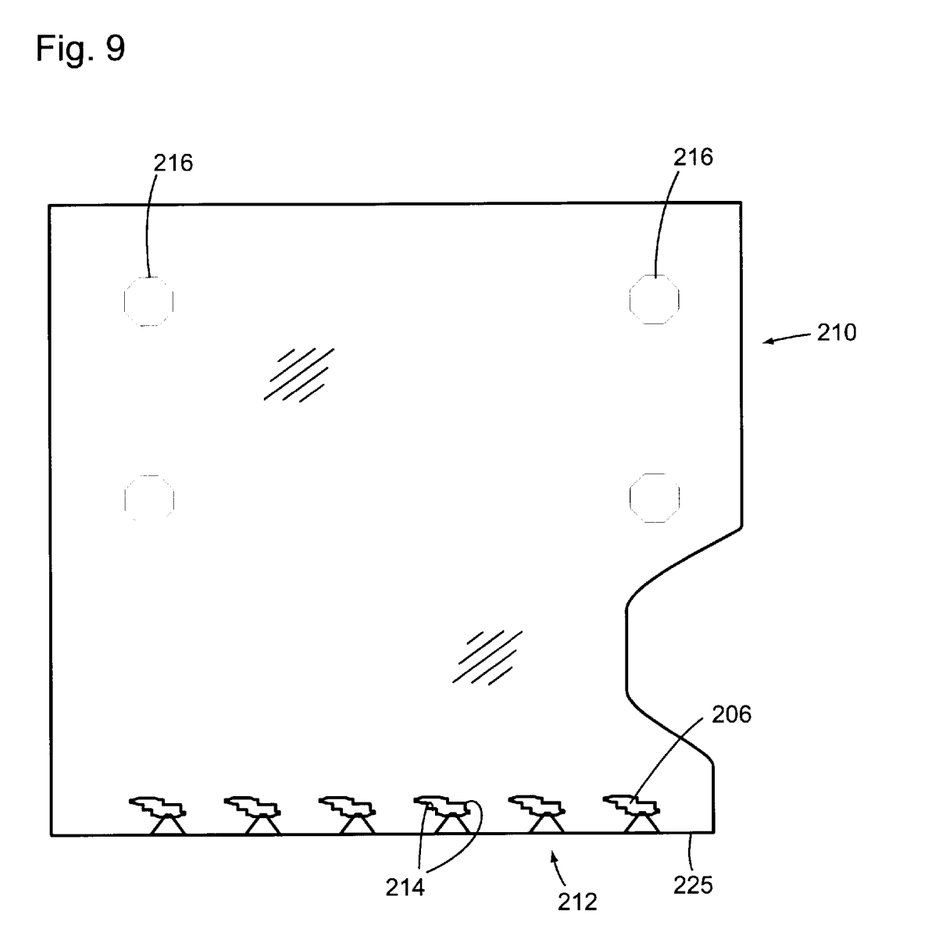
FIG. 9 is a top view of a second part of a guide fixture according to an alternative embodiment of the invention.

FIG. 9 illustrates a second plate 210 of the guide fixture 200. The second plate 210 of the guide fixture 200 includes a plurality of second portions 212 of the guide passages 206. Each second portion 212 of a particular guide passage 206 has walls 214 which define a close fit relationship with a discrete element 52 as the discrete element 52 passes through the second portion 212 of the guide passage 206.

Figure 10:
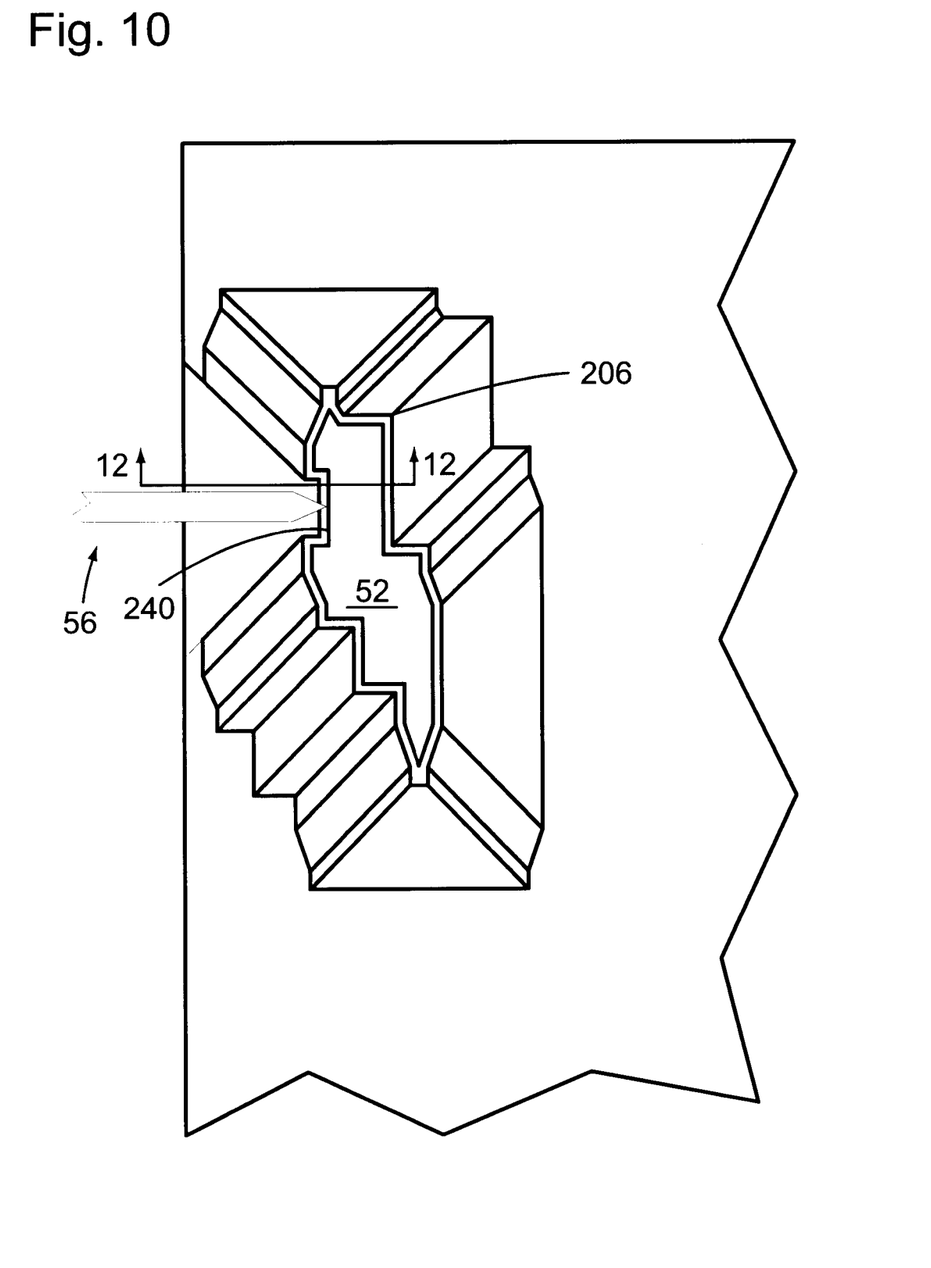
FIG. 10 is a top view of one guide passage according to an alternative embodiment of the invention.
Figure 11:
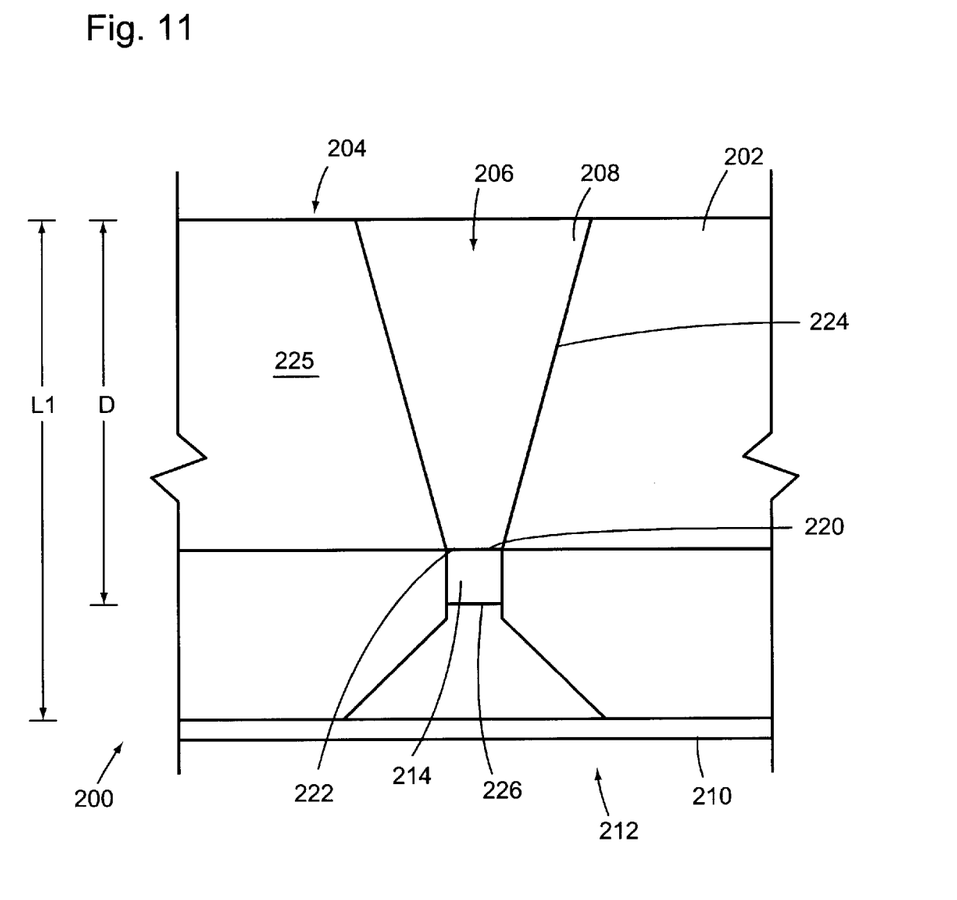
FIG. 11 is a side view of one guide passage according to an alternative embodiment of the invention.

As shown in FIG. 10 and 11, the first plate 202 and the second plate 210 are secured together, preferably via conventional attachment mechanisms, such as bolts, through holes 216 (see FIGS. 8 and 9). The use of two plates 202, 210 is preferred for ease of manufacture. However, the two plates 202, 210 may be instead a single plate. In such a case, the two portions 204, 212 of the guide passage 206 would be defined in the single plate.

Each first portion 204 of the guide passage 206 has a lower open end 220 which is substantially the same shape and size as an opening 222 of a corresponding second portion 212. Each second portion 212 is aligned adjacent with a corresponding first portion 204. Each second portion 212 is also adjacent to and aligned with one of the pockets 48 of the cartridge 10, as shown and described earlier.

A plurality of slots 224 are provided along a side 225 of the guide fixture 200. Each slot 224 extends a selected distance D along a length L1 of a particular guide passage 206. Each slot 224 is configured to receive a portion of the holder 56, preferably the narrow strip adjacent the discrete element 52, as described earlier. A knife edge 226 is fixedly disposed adjacent each slot 224. The distance D is related to the selected position of the knife edge 226 and the length LP of the second passage portion 212. Each slot 224 must accommodate movement of the branch 58 along the guide passage 206 to allow the branch to engage the knife edge 226 in order to assure severing the connection between the branch 58 and the discrete element 52. Although the knife edge 226 is shown as being disposed in the second passage portion 212, the distance D may vary and the knife edge 226 may be located near the first passage portion 204.

Figure 12:
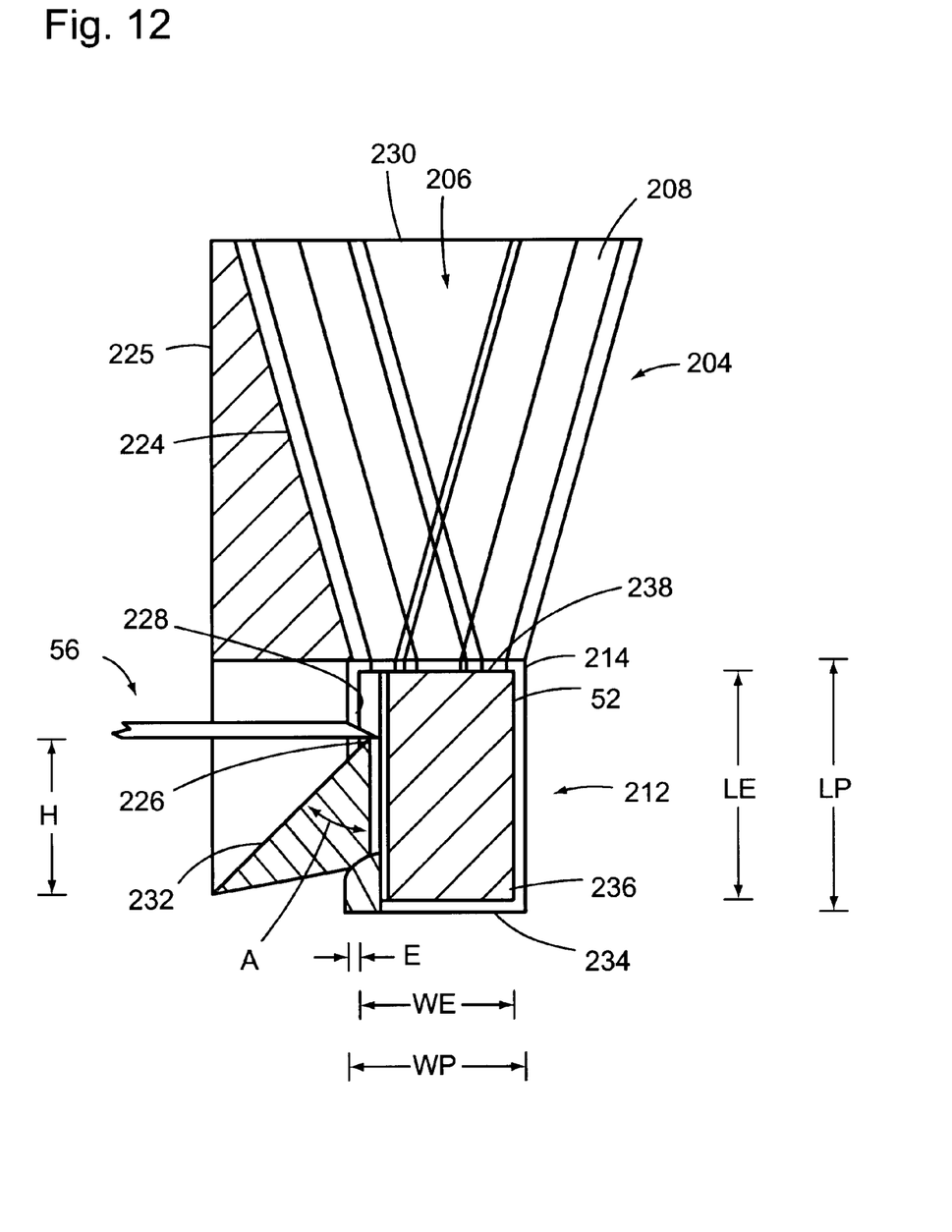
FIG. 12 is a cross-sectional view of one guide passage according to an alternative embodiment of the invention taken along line 12—12 of FIG. 10.

As is seen most clearly in FIG. 12, each of the plurality of knife edges 226 is configured to engage a holder portion 228 near the end of each branch 58 adjacent to a particular discrete element 52 after the discrete element 52 has been inserted into the guide passage 206. The knife edge 226 is oriented away from the cartridge 10 (not shown), towards the top 230 of the guide passage 206. Each knife edge 226 is formed at an angle A, preferably about 45 degrees, between a wall 214 of the guide passage and an angled portion 232 of the guide fixture 200. The positioning of the knife edge 226 reflects the size and shape of the discrete element 52 passing through the guide passage 206 and its point of attachment 228 to a branch 58 of the holder 56. In the preferred embodiment shown in FIG. 10, the discrete element 52 includes an indentation 240 which is about 0.007 inches in depth. The knife edge 226 extends into the guide passage 206 to be closely adjacent a side wall of the discrete element 52 to separate the discrete element 52 from the end 228 of a branch 58 of a holder 56 as closely as possible to the discrete element 52. This close adjacency reduces the remnant of the holder 56 which remains on the discrete element 52 after the discrete element 52 is separated from the holder 56.

As mentioned above, the walls 214 of the second portion 212 of the guide passage 206 define a close fit relationship with a respective discrete element 52. The width WP of the second portion 212 of the guide passage 206 is preferably about 0.001 inch greater than the width WE of the discrete element 52. The length LP of the second portion 212 of the guide passage 206 is preferably about the same as the length LE of the discrete element 52. This provides greater stability during the separation step and assures correct alignment of the discrete element 52 over a pocket 48 in the cartridge 10.

Similarly, the knife edge 226 is preferably spaced a selected distance H from the bottom 234 of the guide passage 206. The selected distance H should be selected to be appropriate to engage the branch 58 near the discrete element 52 when the bottom 236 of the discrete element 52 is close to the bottom 234 of the guide passage 206, as is shown. As the discrete elements 52 and holder 56 are currently constructed, the preferred selected distance H is between about ½ and ⅔ the length LE of the discrete element 52.

Once one of the discrete elements 52 has been placed into one of the guide passages 206 and a holder portion 228 near the corresponding discrete element 52 rests against one of the knife edges 226, the switch 24 is actuated as described above to urge the plunger plate 30 downward to reciprocate the plurality of plungers 34 mounted thereon. Each plunger 34 is aligned with one guide passage 206. Each plunger 34 is configured to force one of the discrete elements 52 though a corresponding guide passage 206 and into a corresponding pocket 48 of the cartridge 10. As a plunger 34 contacts the top surface 238 of a respective discrete element 52 and drives the discrete element 52 through the guide passage 206, the corresponding holder portion 228 near the discrete element 52 engages the corresponding knife edge 226, thereby separating the discrete element 52 from the holder 56.

An additional modification to the apparatus shown in FIGS. 1–7 and described in connection therewith, which is desirable if the other modifications as shown in FIGS. 8–12 are used, is the addition of a stabilizing finger 250, which is shown most clearly in FIGS. 1–3. The stabilizing finger 250 projects generally upwardly from the base 16 and support block 38 of the apparatus 12. As seen most clearly in FIG. 3, the stabilizing finger 250 contacts the straight bar 60 of the tree or holder 56 once the discrete elements 52 have been inserted into the guide passages 206. It is particularly important to use the stabilizing finger 250 if single staple drivers are the discrete elements 52 to be inserted into the cartridge 10. This is due to the minute size of such a discrete element 52. In general, the smaller the discrete element 52, the easier it is to misalign the discrete element 52 in the guide passage 206. If the discrete elements 52 are not properly aligned in the guide passages 206, the discrete elements 52 will not be properly inserted into the cartridge 10, if they are inserted at all.

With a holder 56 of a configuration which is standard in the industry, the branches 58 are molded at an angle with the straight bar 60, rather than the entire holder 56 being generally planar. Because of this angle, best seen in FIG. 3, the stabilizing finger 250 extends away from the support block 38 until it is slightly below the top 252 of the guide fixture 202. The stabilizing finger 250 is configured to have a height appropriate to a particular holder 56 and guide fixture 202 to ensure that the stabilizing finger 250 contacts the holder 56 only when the discrete elements 52 are fully inserted into the guide passages 206 and a portion of the holder 56 contacts the knife edge 226. If the stabilizing finger 250 does not extend an appropriate distance from the base 16, the discrete elements 52 are not inserted properly. If the stabilizing finger 250 extends too great or too small a distance, the straight bar 60 will engage the stabilizing finger 250 and will tend to place the discrete elements 52 at an angle within the guide passages 206, a result which is not desirable. One of ordinary skill in the art is able to select an appropriate distance for the guide finger 250 to extend from the support block 38 without undue experimentation, based on the particular size of the discrete elements 52 and the related size of the guide passages 206, in addition to the angle and length of the branches 58.

The stabilizing finger 250 may be attached to the base 16, but is preferably secured to the support block 38. The stabilizing finger 250 may be made of a variety of materials and may be attached in any way which is conventional in the art, as long as the stabilizing finger 250 has sufficient stability to aid in the proper insertion of the discrete elements 52 into the guide passages 206.

While certain preferred embodiments of the present invention have been disclosed in detail, it is to be understood that various modifications may be adopted without departing from the spirit of the invention or scope of the following claims.

What is claimed is:

1. Apparatus for separating discrete elements from a holder and filling a cartridge having at least one pocket configured to receive at least one discrete element, comprising:
   (a) a guide fixture which includes
      (1) a guide passage defined therein including
         (a) a first portion configured to receive the one discrete element, the first portion having converging tapered walls; and
         (b) a second portion which is adjacent to and aligned with both the first portion and the pocket of the cartridge, the second portion having walls defining a close fit relationship with the one discrete element passing along a length of the second portion;
      (2) a slot provided along a side of the guide fixture extending a selected distance along a length of the guide passage, the slot being configured to receive a portion of the holder; and
      (3) a knife edge disposed adjacent the slot and configured to engage a holder portion near the discrete element after the discrete element has been inserted into the guide passage; and
   (b) a reciprocally mounted plunger aligned with the guide passage and configured to force the discrete element through the guide passage and into the pocket of the cartridge, thereby causing the holder portion near the discrete element to engage the knife edge and separate the discrete element from the holder.

2. An apparatus for separating discrete elements from a holder and filling a cartridge with the discrete elements according to claim 1, wherein the discrete elements are staple drivers.

3. An apparatus for separating discrete elements from a holder and filling a cartridge with the discrete elements according to claim 1, wherein the second portion of the guide passage has a width and the discrete element has a width, the width of the second portion being about $1/1000$ inch greater than the width of a respective discrete element.

4. An apparatus for separating discrete elements from a holder and filling a cartridge with the discrete elements according to claim 1, wherein the knife edge is oriented away from the cartridge and forms a 45 degree angle with respect to an inner wall of the guide passage.

5. An apparatus for separating discrete elements from a holder and filling a cartridge with the discrete elements according to claim 1, wherein the guide fixture is a single part.

6. An apparatus for separating discrete elements from a holder and filling a cartridge with the discrete elements according to claim 1, wherein the guide fixture includes a first plate and a second plate and the first portion of the guide passage is formed in the first plate and the second portion of the guide passage formed in the second plate, the plates being secured to one another.

7. An apparatus for separating discrete elements from a holder and filling a cartridge with the discrete elements according to claim 1, wherein the first portion of the guide passage terminates in an open end which is substantially the same shape and size as an open upper end of the second portion.

8. An apparatus for separating discrete elements from a holder and filling a cartridge with the discrete elements according to claim 1, wherein the second portion has a length and each discrete element has a length, the length of the second portion being at least about one-half the length of the discrete element.

9. An apparatus for separating discrete elements from a holder and filling a cartridge with the discrete elements according to claim 8, wherein the knife edge is spaced a selected distance from a lower end of the guide fixture, the selected distance being about one-half the length of the discrete element.

10. Apparatus for separating discrete elements from a holder and filling a cartridge with the discrete elements, comprising:
   (a) a cartridge which includes a pocket defined therein, the pocket being configured to receive one discrete element;
   (b) a guide fixture which includes
      (1) a guide passage defined therein including
         (a) a first portion configured to receive the one discrete element, the first portion having converging tapered walls; and
         (b) a second portion which is adjacent to and aligned with both the first portion and the pocket of the cartridge, the second portion having walls defining a close fit relationship with the one discrete element passing along a length of the second portion;
      (2) a slot provided along a side of the guide fixture extending a selected distance along a length of the guide passage, the slot being configured to receive a portion of the holder; and
      (3) a knife edge disposed adjacent the slot and configured to engage a holder portion near the discrete element after the discrete element has been inserted into the guide passage; and
   (c) a reciprocally mounted plunger aligned with the guide passage and configured to force the discrete element through the guide passage and into the pocket of the cartridge, thereby causing the holder portion near the discrete element to engage the knife edge and separate the discrete element from the holder.

11. An apparatus for separating discrete elements from a holder and filling a cartridge with the discrete elements according to claim 10, wherein the discrete elements are staple drivers.

12. An apparatus for separating discrete elements from a holder and filling a cartridge with the discrete elements according to claim 10, wherein the second portion of the guide passage has a width and the discrete element has a width, the width of the second portion being about $1/1000$ inch greater than the width of a respective discrete element.

13. An apparatus for separating discrete elements from a holder and filling a cartridge with the discrete elements according to claim 10, wherein the knife edge is oriented away from the cartridge and forms a 45 degree angle with respect to an inner wall of the guide passage.

14. An apparatus for separating discrete elements from a holder and filling a cartridge with the discrete elements according to claim 10, wherein the guide fixture is a single part.

15. An apparatus for separating discrete elements from a holder and filling a cartridge with the discrete elements according to claim 10, wherein the guide fixture includes a first plate and a second plate and the first portion of the guide passage is formed in the first plate and the second portion of the guide passage formed in the second plate, the plates being secured to one another.

16. An apparatus for separating discrete elements from a holder and filling a cartridge with the discrete elements according to claim 10, wherein the first portion of the guide passage terminates in an open end which is substantially the same shape and size as an open upper end of the second portion.

17. An apparatus for separating discrete elements from a holder and filling a cartridge with the discrete elements according to claim 10, wherein the second portion has a length and each discrete element has a length, the length of the second portion being at least about one-half the length of the discrete element.

18. An apparatus for separating discrete elements from a holder and filling a cartridge with the discrete elements according to claim 17, wherein the knife edge is spaced a selected distance from a lower end of the guide fixture, the selected distance being about one-half the length of the discrete element.

19. Apparatus for separating discrete elements from a holder and filling a cartridge with the discrete elements, comprising:
  (a) a cartridge which includes a plurality of pockets defined therein, each pocket being configured to receive one discrete element;
  (b) a guide fixture which includes
    (1) guide passages defined therein, each guide passage including
      (a) a first portion configured to receive the one discrete element, the first portion having converging tapered walls; and
      (b) a second portion which is adjacent to and aligned with both the first portion and one pocket of the cartridge, the second portion having walls defining a close fit relationship with the one discrete element passing along a length of the second portion;
    (2) a plurality of slots provided along a side of the guide fixture, each slot extending a selected distance along a length of one guide passage, each slot being configured to receive a portion of the holder; and
    (3) a plurality of knife edges, each knife edge being disposed adjacent one of the slots and configured to engage a holder portion near the discrete element; and
  (c) a plurality of reciprocally mounted plungers, each plunger being aligned with one guide passage and configured to force one discrete element through the one guide passage and into one of the pockets of the cartridge, thereby causing one holder portion near the discrete element to engage one knife edge to separate the discrete element from the holder.

20. An apparatus for separating discrete elements from a holder and filling a cartridge with the discrete elements according to claim 19, wherein each second portion has a length and each discrete element has a length, the length of one second portion being about the same as the length of one discrete element.

21. A process for separating discrete elements from a holder and filling a cartridge having at least one pocket configured to receive at least one discrete element, comprising:
  (a) placing a portion of the holder in a slot provided along a side of a guide fixture substantially simultaneously with positioning one discrete element attached to the holder in a guide passage provided in the guide fixture;
  (b) moving the holder in the slot until a holder portion adjacent the discrete element nears a knife edge disposed adjacent the slot;
  (c) aligning a reciprocally mounted plunger with the guide passage; and
  (d) reciprocating the plunger to force the discrete element through the guide passage and the holder portion into engagement with the knife edge, thereby separating the discrete element from the holder, and disposing the discrete element in the one pocket.

* * * * *